Sept. 25, 1962 H. M. TIRET Plant Pat. 2,174
FUCHSIA PLANT
Filed Oct. 30, 1961
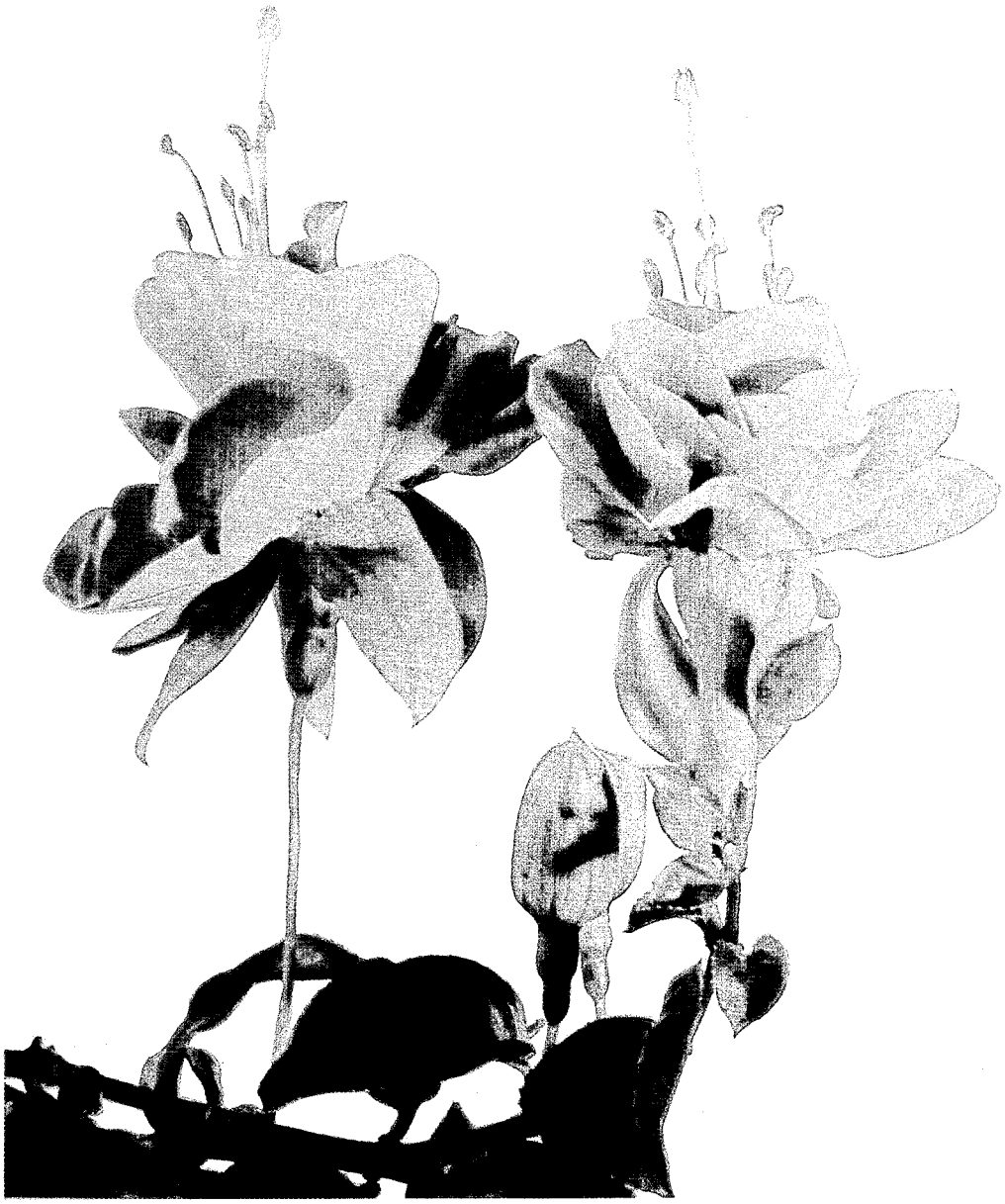

United States Patent Office

Plant Pat. 2,174
Patented Sept. 25, 1962

2,174
FUCHSIA PLANT

Horace M. Tiret, 2126 Taraval St., San Francisco, Calif.

Filed Oct. 30, 1961, Ser. No. 148,781
1 Claim. (Cl. 47—60)

This invention relates to a new and improved fuchsia plant, the principal new and different characteristic of which is the exceptional size of bloom and color combined with the classical form of the flower, unlike any other fuchsia plant.

The accompanying drawing illustrates the plant in bloom and the aforementioned new and different characteristics.

The fuchsia plant was derived as a hybrid from a seedling (unpatented) not introduced to the trade, namely 8–43–9 (figures representing applicant's own breeding symbols) and Papa Bleuss, Plant Patent No. 1,620. The plant has been asexually reproduced at Colma, California, but cuttings which retained the characteristics of the parent fuchsia plant.

The plant is a vigorous, upright grower. It is a heavy early bloomer.

In the accompanying drawings, the figure shows a typical branch tip represented in approximate actual size.

A detailed description of the new variety of fuchsia plant follows (all measurements approximate):

*Habit of growth.*—Vigorous, upright variety. Early, consistent bloomer and profuse self-brancher.

*Foliage.*—The leaves are dark green, medium small in size, medium veined surface. The mature leaf is approximately 3″ in length and 2″ in width at the broadest point. Texture of the leaf is crinkly (medium). Branches are dark reddish-brown.

*Buds.*—Color of buds is Crimson (British Horticultural Color Chart #22/1) with slight green tips. Length from ovary is approximately 1¾″. Width at the broadest point is 1″.

*Ovary.*—Color of the ovary is green. Length is ¼″. Width at the broadest point, at maturity, is ¼″.

*Sepals.*—There are 4 sepals, each 1⅝″ in length and 1″ in width at the broadest point. Form is broad and recurred. The texture of the underside is crepe and the outer surface is smooth and satiny. Color of the underside is Neyron Rose (British Horticultural Color Chart #623) with green tips. The outside color is Crimson #22/1.

*Tube.*—Medium and medium broad. Length is ⅝″, width 5/16″ at broadest point. Color is Crimson.

*Stamens.*—There are 8 stamens, colored flesh, with rose anthers. Form is medium slender, length is 2″.

*Pistil.*—The style is 3″ in length, 1/32″ in width. The color is Neyron Rose, the stigma flesh color.

*Petals.*—Color of petals is Heliotrope (British Horticultural Color Chart #636/2) outer petals are marbled with Neyron Rose (British Horticultural Color Chart 623/1). The main petals of a mature flower are Heliotrope veined with Neyron Rose.

The petals are 25 in number. They are large with fully open corolla. Position of the petals is vertical for the center and horizontal for the outer, which results in a flaring form. The diameter of the fully open mature flower is 3¾″. The large petals are 1¾″ in length and width. The texture is smooth.

*Parentage.*—Applicant's own seedlings, namely 8–43–9 (unpatented) not introduced to the trade—applicant's own breeding symbols) and Papa Bleuss, Plant Patent No. 1,620.

Having thus disclosed my discovery, I claim:

A new and distinct variety of fuchsia plant, substantially as herein shown and described, characterized by the Heliotrop coloring of the petals, exceptional size of the blooms, combined in a classic form in a fuchsia plant which has vigorous, upright growth characteristics.

No references cited.